US006340408B1

(12) United States Patent
Norlander

(10) Patent No.: US 6,340,408 B1
(45) Date of Patent: Jan. 22, 2002

(54) METHOD OF PREPARATION OF A FLUFFED PULP TO BE USED IN ABSORBENT PRODUCTS

(75) Inventor: Leif Norlander, Falun (SE)

(73) Assignee: Stora Kopparbergs Bergslags Aktiebolag (Publ), Falun (SE)

( * ) Notice: Subject to any disclaimer, the term of this patent is extended or adjusted under 35 U.S.C. 154(b) by 0 days.

(21) Appl. No.: 09/155,244

(22) PCT Filed: Apr. 10, 1997

(86) PCT No.: PCT/SE97/00561

§ 371 Date: Sep. 24, 1998

§ 102(e) Date: Sep. 24, 1998

(87) PCT Pub. No.: WO97/39188

PCT Pub. Date: Oct. 23, 1997

(30) Foreign Application Priority Data

Apr. 15, 1996 (SE) ................................. 9601412

(51) Int. Cl.$^7$ ............................. D21C 1/02; D21H 1/08; D21H 21/22; D21H 17/66
(52) U.S. Cl. ............................. 162/20; 162/24; 162/25; 162/79; 162/181.5
(58) Field of Search ............................. 162/79, 20, 25, 162/26, 24, 181.2, 181.3, 181.5

(56) References Cited

FOREIGN PATENT DOCUMENTS

| SU | 1261996 A1 | 10/1986 |
|---|---|---|
| WO | 91/05106 | 4/1991 |

*Primary Examiner*—Steve Alvo
(74) *Attorney, Agent, or Firm*—Nixon & Vanderhye

(57) ABSTRACT

A method for the preparation of cellulosic pulp capable of being defibrated (fluffed) for the manufacture of an absorbent material intended to be incorporated as a component in absorbent products. A stock of cellulosic fibres in aqueous suspension is pH-adjusted to 4<pH<8, that at least any water-soluble, non-polymeric aluminium salt is added to the stock, said salt in aqueous solutions at said pH forming at least any hydrocomplex with aluminium of the type $Al(OH)_n^x$, where n is a number between 1 and 3, and x is o, + or 2+, that said salt in aqueous solution is caused to act on the cellulosic fibres in said suspension at said pH during a period of time of at least 2 min, and that the fibre pulp thereafter is formed to a web, which is dewatered and dried. The invention also relates to the prepared cellulose pulp as such and to its use in absorbent products.

15 Claims, 7 Drawing Sheets

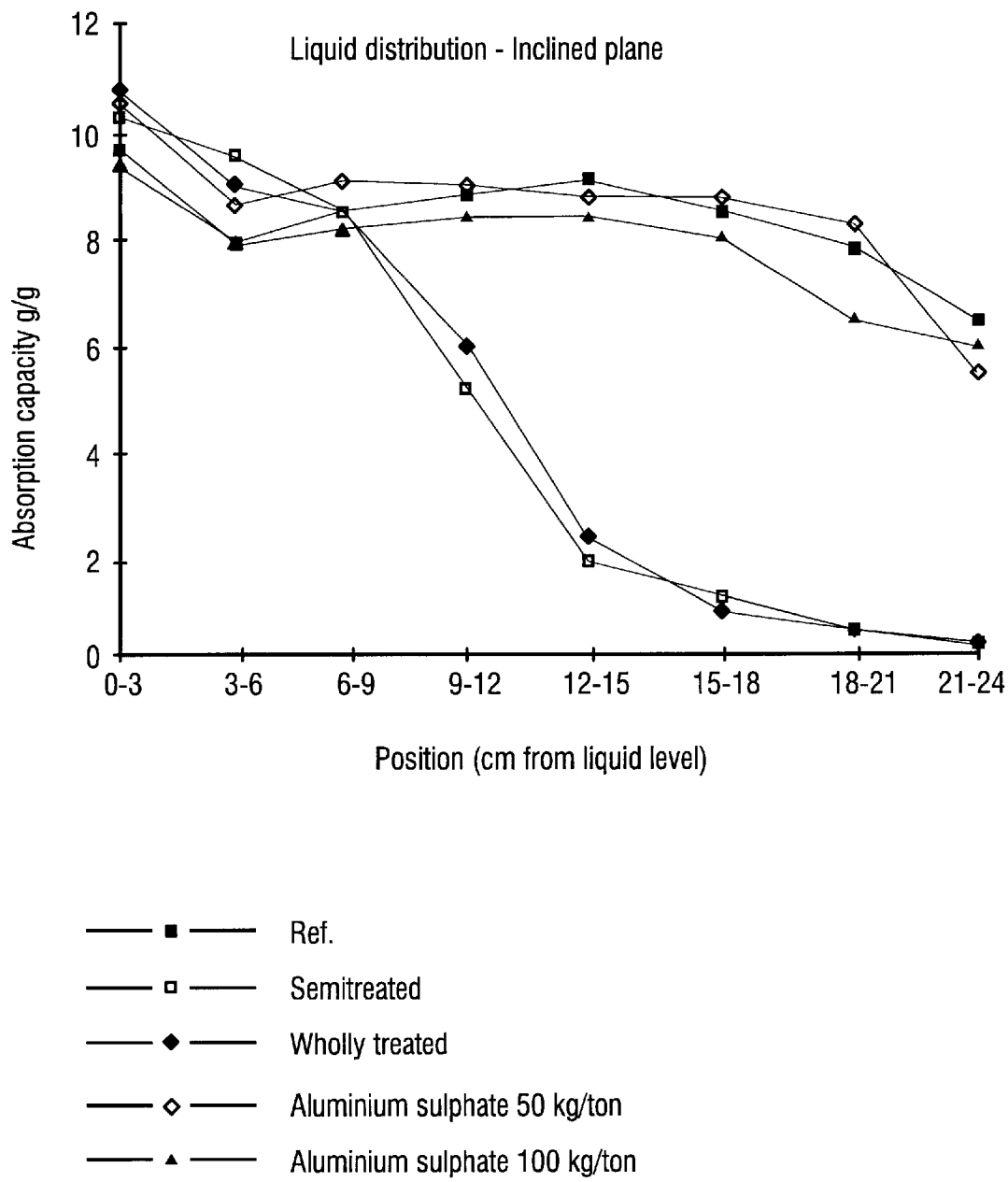

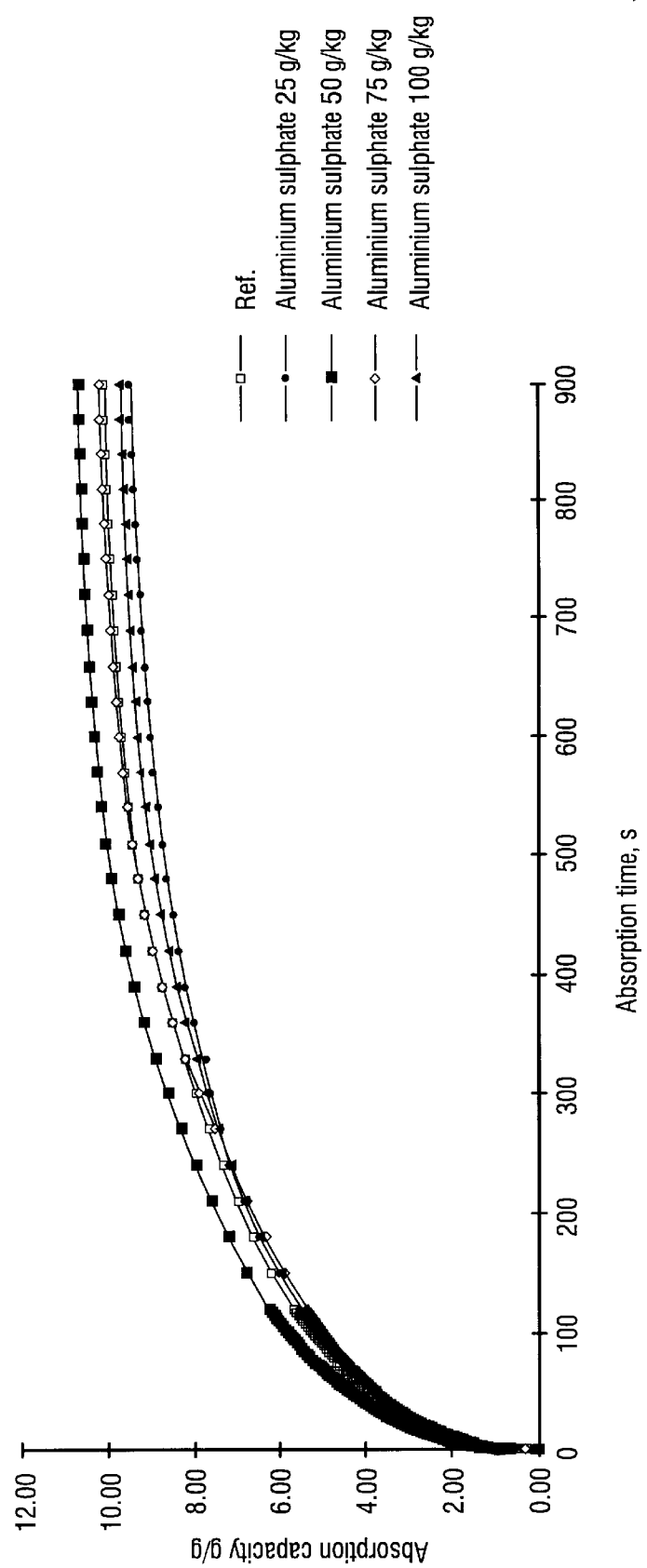

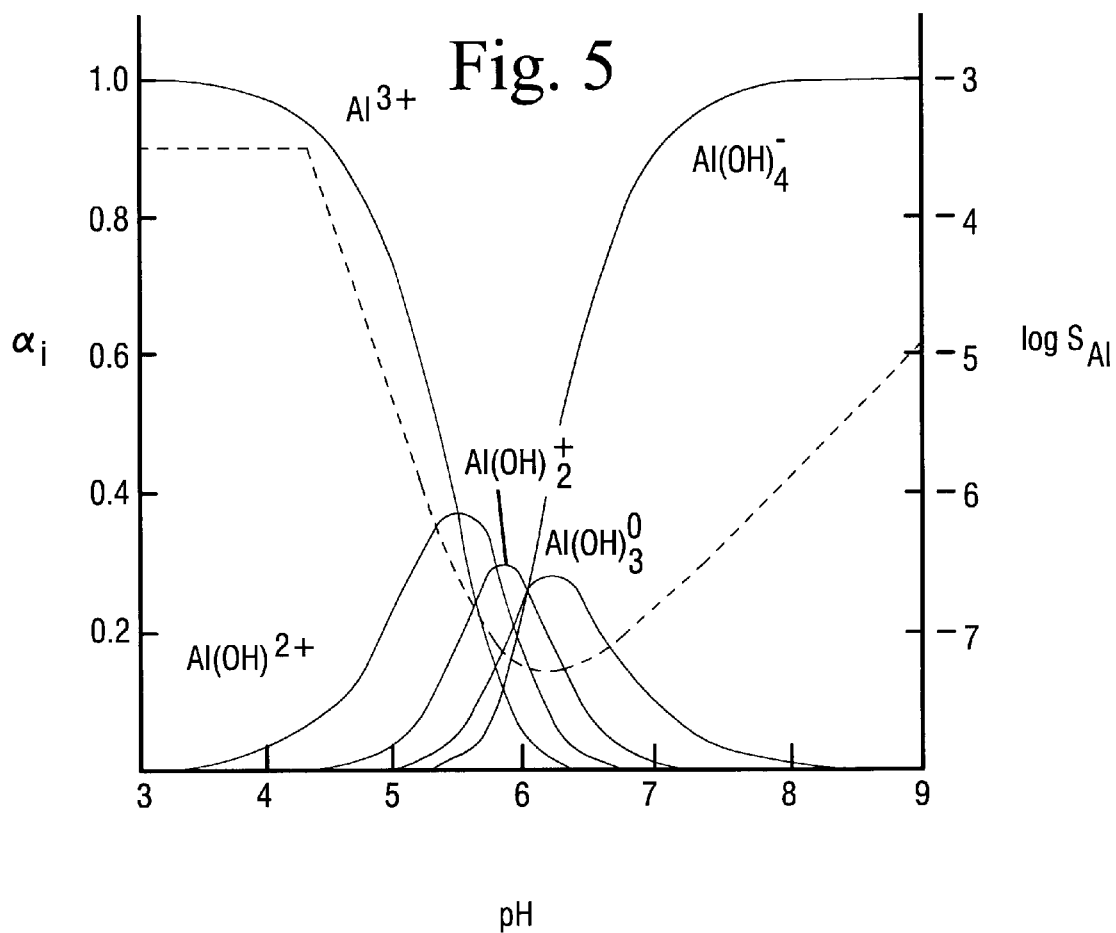

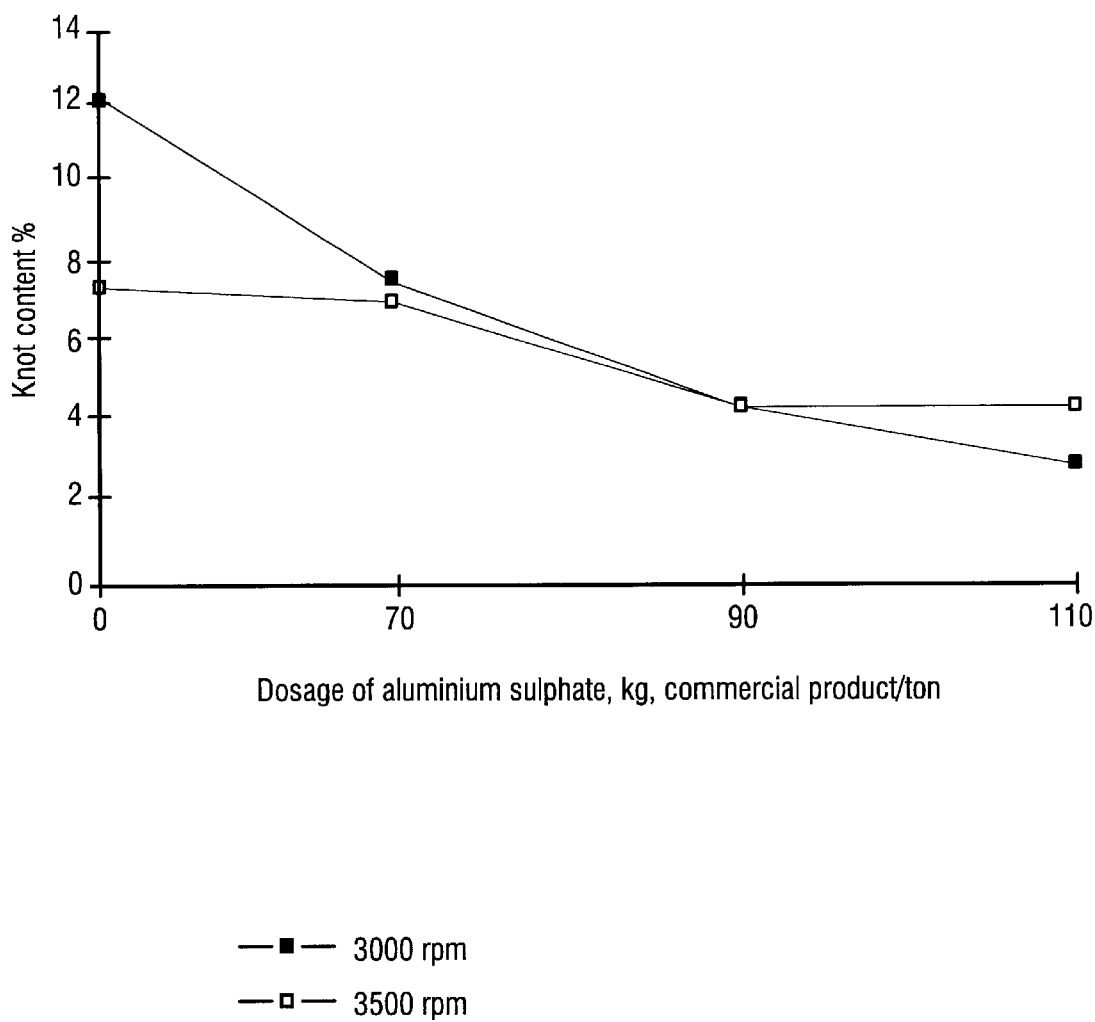

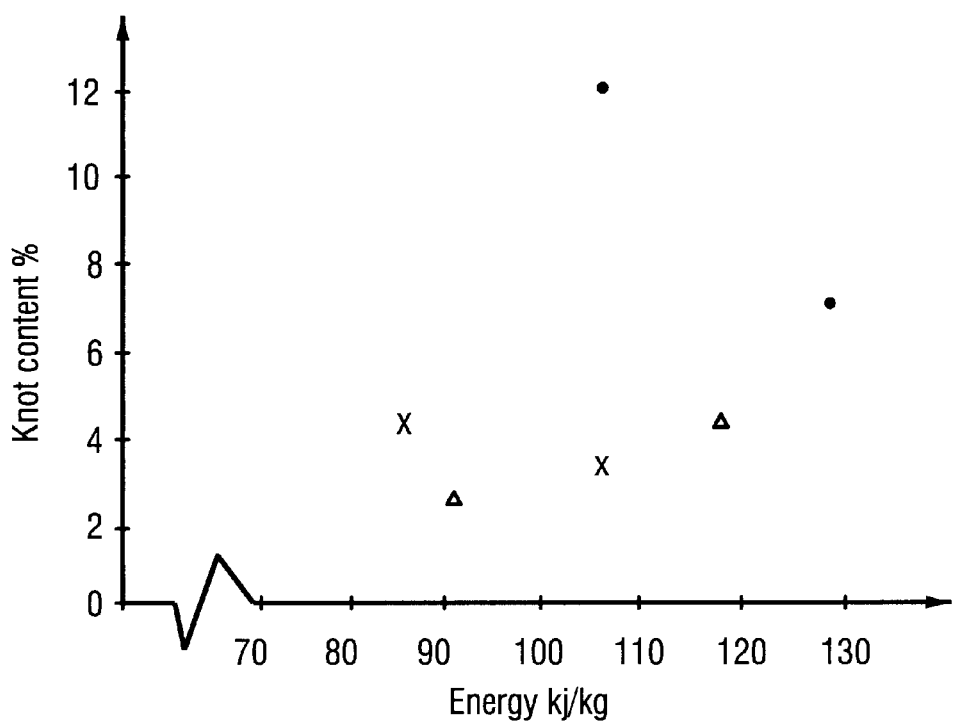

METHOD OF PREPARATION OF A FLUFFED PULP TO BE USED IN ABSORBENT PRODUCTS

TECHNICAL FIELD

The invention relates to a method of preparation of a cellulosic pulp capable of being defibrated (fluffed) for the manufacture of an absorbent material intended to be incorporated as a component in absorbent products. The invention also relates to the cellulosic pulp, the absorbent material, and the absorbent product.

BACKGROUND OF THE INVENTION AND STATE OF THE ART

Chemical pulp, particularly bleached chemical pulp, and bleached and unbleached chemothermomecanically manufactured pulp, so called CTMP, are used as materials for the manufacture of absorbent materials intended to be incorporated as a main component in absorbent products, such as diapers, sanitary towels, incontinence protections and other hygiene products as well as some type of serviettes and the like.

Bleached chemical pulp has a good wettability and initially a good liquid distribution capacity and hence a high absorbency rate. On the other hand, it is difficult to defibrate properly because of its high fibre to fibre binding capacity. This is a drawback, i.e. because a better separation of fibres gives a higher network strength and hence increased strength to the absorbent product. In connection herewith should be mentioned that an increased strength is an increasingly important feature and in many cases a critical feature for applications such as napkins and sanitary towels, as there is a tendency to reduce the content of fluff pulp in such absorbent products in order to make them thinner. Often, debonders therefore are added to chemical pulp in order to improve the deliberation efficiency. This, however, impairs the liquid distribution capacity of the defibrated pulp and hence its absorbency rate, which is a drawback.

As far as CTMP is concerned, the conditions are different. That kind of pulp is not as wettable as chemical defibrated pulp is in its defibrated condition and has therefore usually not as good distribution features as the latter one. On the other hand, the defibration features are more favorable, which reduces the need of debonders.

In SE 500 871 experiments are described which show that the distribution features and the absorbency rate of CTMP fluff pulp can be improved by impregnation of the fibres in aqueous suspension with an aluminium salt in aqueous solution at a pH which preferably should lie in the range 8.5 to 9.5, particularly at pH 9. According to SE 500 858 of the same applicant, the improved distribution capacity and absorbency rate are attributed to the formation of a porous layer of hydrophilic chemicals attached to the fibre surface, which considerably increases the specific surface of the fibres is EP 500 858 it is recommended that aluminium ions are added in the form of polyaluminium chloride or sulphate, aluminium phosphate or sodium abominate or mixtures thereof, and it is also stated that polyaluminium ions appear to function more efficiently than ordinary aluminium ions. EP 500 571recommends polyaluminium chloride, polyaluminium sulphate, sodium aluminate, and other basic aluminium compounds, but describes substantially only experiments made with additions of polyaluminium chloride and polyaluminium sulphate to CTMP at pH 9. In one case, CTMP fibres were impregnated with water-glass, which was precipitated at pH 9 with alum and polyaluminium chloride. Any significant increase of the absorbency rate could not be noticed in the case of alum and nor any increase of the network strength. Only in SE 500 871 experiments with chemical pulp are described, examples 1 and 17. At these experiments, the pulp was impregnated with polyaluminium sulphate at pH 3 and pH 11, and with polyaluminium chloride at pH 9, respectively. In both cases the absorbency rate was increased. In the first case, however, not clear at which pH, also the network strength was increased to some degree: from 3.7 to 4.3 N.

BRIEF DISCLOSURE OF THE INVENTION

It is a primary object of the invention to improve the defibration efficiency of chemical pulp in order to reduce the knot content and to increase the network strength of chemical pump by improved separation of the fibres. Due to the improved defibration efficiency also the defibration energy supplied at the defibration can be reduced and the need of debonders be eliminated or significantly reduced. It is also an object to provide a cellulosic pulp with good absorption features, including distribution features and a high absorbency rate, particularly an improved distribution capacity as compared with chemical fluff pulp, the defibration efficiency of which has been improved through the addition of organic debonder.

Experiments have also been made with CTMP, which indicate that the method of the invention can improve the absorbency rate of that type of pulp significantly, however not noteworthy its defibration efficiency in terms of reduced defibration energy and/or increased network strength.

The above objects and effects can be achieved therein that the invention is characterised by what is stated in the appending claims. Further characteristic features and aspects of the invention will be apparent from the following description of performed experiments and by the discussion in connection thereto.

BRIEF DESCRIPTION OF DRAWINGS

In the following description of performed experiments, reference will be made to the appending drawings, in which

FIG. 3A shows the distribution capacity of different, tested pulps;

FIG. 3B shows the absorption capacity versus absorption time for various additions of aluminium sulphate;

FIG. 5 is a diagram from Paper Chemistry, An introduction, Dan Eklund, Tom Lindström, DT Paper Science Publications, p 134–144;

FIG. 6 shows knot content versus added amount of aluminium sulphate at pilot experiments; and FIG. 7 shows know content related to defibration energy at different dosages of aluminium sulphate.

PERFORMED EXPERIMENTS

At the experiments bleached chemical fluff pulp fibres produced according to the sulphate pulp method was treated and tested. The fibre raw material was Nordic coniferous wood. A minor experiment also was made with CTMP fluff pulp.

At a first experiment series there were used couch strips, which never had been dried, of which sheets were made in sheet mold according to standard method in laboratory. The pulp concentration was 0.7%. The addition of aluminium sulphate, $Al_2(SO_4)_3$, and various salts, respectively, was made at about 1.5% pulp concentration before final dilution in sheet mold. The aluminium sulphate chemical was aluminium sulphate in the form of a commercial product, which has 75% dry content, if not otherwise indicated. The aluminium sulphate, which was used in the experiments, was manufactured by Kemira AB. Any pH-adjustments were made with $H_2SO_4$ or NaOH, respectively.

Distribution tests were carried out on inclined plane with 30° inclination according to a method which is developed and standardised by the applicant. Briefly, the method implies that the test sample is placed on the inclined plane and that the lower edge of the test sample is caused to contact the test liquid. The amount of liquid which is absorbed is registered by time unit through weighing during a time period of 900 s, whereafter the test sample is cut and strips are cut cross-wise relative to the flow direction and are weighed. Knot content was registered according to SCAN-CM 37.85. Network strength was tested by means of a measurement apparatus of type Alwetron at the rate 60 mm/min on test samples, 1 g, made according to SCAN 33:80. Other fluff properties were evaluated by standard methods which are described in WO93/16228 of the same applicant. The defibration was made at a laboratory scale by means of a hammer hammer mill of type Kamas. Reported defibration energy is net energy. The results from initial experiments are shown in Table 1.

TABLE 1

| Aluminum sulphate usage | g/kg | 0 | 50 | 75 | 100 |
|---|---|---|---|---|---|
| pH | | 6.5 | 6.5 | 6.5 | 6.5 |
| Ash content | % | 0.20 | 1.1 | 1.6 | 2.1 |
| Surface weight | g/m² | 816 | 834 | 834 | 826 |
| Thickness | mm | 1.50 | 1.49 | 1.50 | 1.46 |
| Density | kg/m³ | 543 | 559 | 556 | 554 |
| Defibration energy 3500 rpm | kJ/kg | 156 | 151 | 122 | 111 |
| Network strength | N/lg | 6.8 | 6.8 | 7.5 | 7.7 |
| Knot content | % | 11.6 | 7.4 | 3.7 | 1.8 |
| Distribution on inclined plane, 30° inclination | | | | | |
| Density of test sample | kg/m³ | 155 | 152 | 150 | 154 |
| Absorption capacity | | | | | |
| 0–3 cm | g/g | 9.5 | 10.4 | 9.8 | 9.3 |
| 3–6 cm | g/g | 8.0 | 8.6 | 8.2 | 8.0 |
| 6–9 cm | g/g | 8.6 | 9.0 | 8.6 | 8.4 |
| 9–12 cm | g/g | 8.9 | 9.0 | 8.9 | 8.4 |
| 12–15 cm | g/g | 9.0 | 8.8 | 9.0 | 8.6 |
| 15–18 cm | g/g | 8.3 | 8.6 | 8.8 | 8.0 |
| 18–21 cm | g/g | 7.8 | 8.1 | 8.1 | 6.6 |
| 21–24 cm | g/g | 6.5 | 5.6 | 6.5 | 6.0 |

Figure 1:
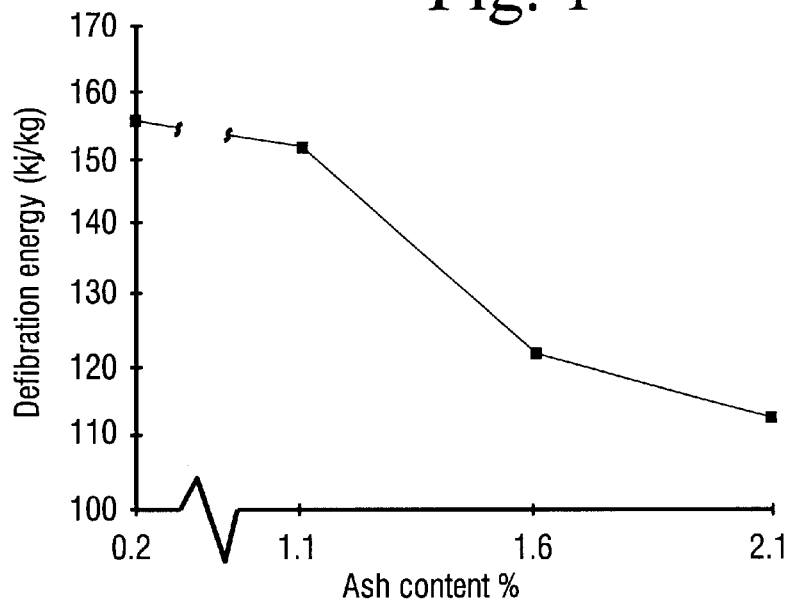
FIG. 1 and FIG. 2 show defibration energy and knot content, respectively, versus ash content at experiments performed at laboratory scale.
Figure 2:
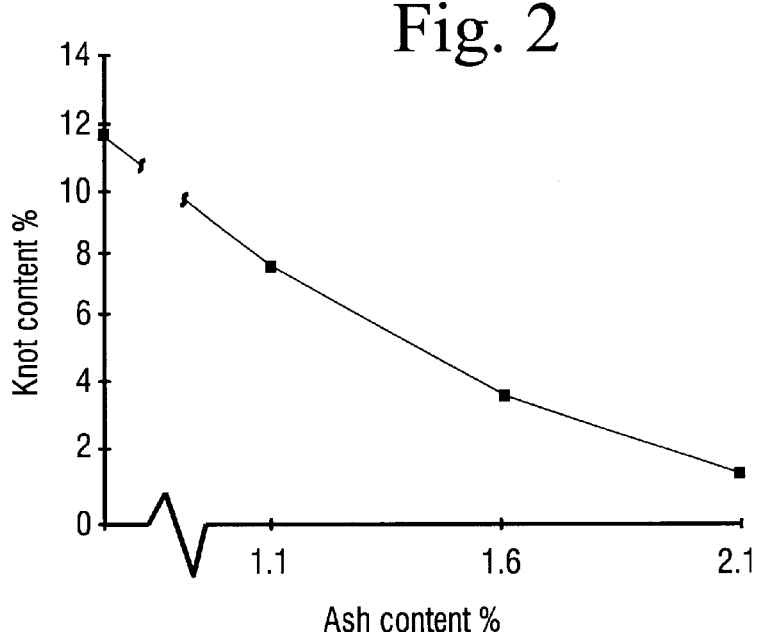

From Table 1 is evident that aluminium sulphate has a favorable impact on the defibration result. A substantial reduction of knot content and defibration energy is achieved at a large addition of aluminium sulphate, 75 to 100 kg/ton, in the form of a commercial product having a dry content of 75%. The improved separation of the fibres also gave rise to an increased network strength at a maintained absorption capacity at the measurement of liquid distribution on inclined plane. The ash content is a measure of the amount of aluminium which has been retained by the fibres. The defibration energy and the knot content versus the ash content and hence also versus the addition of aluminium sulphate also are shown by the charts in FIG. 1 and FIG. 2.

The wettability of the aluminium sulphate treated fibres in terms of liquid distribution on inclined plane was also compared with fibres which were treated with organic debonders. The comparison was made with wholly- and semi-treated commercial fluff pulp) Stora Fluff), which contains quarternary ammonium compounds (Berocell 509-Eka Nobel), which is a today conventional type of debonder. The wholly- and semi-treated fluff pulp had been treated with 2 and 4 kg/ton, respectively, of said debonder. Also completely untreated fluff pulp of type Stora Cell EC01, in the following denoted Ref, is included in this comparative test. The measured distribution values are illustrated in FIG. 3A. The graphs in FIG. 3A show that the untreated fluff pulp and the aluminium sulphate treated pulps had essentially equally good distribution capacities, clearly superior to those of the debonder treated fluff pulps.

The experiments which are reported in Table 1 were carried out on fluff pulp sheets, which had been sheeted at pH 6 to 7. In order to investigate the role of the pH value for the achievement of the improved defibration properties derived by the addition of aluminium sulphate, there were also carried out experiments with lower and higher pH values. In all the experiments, aluminium sulphate was added in an amount corresponding to 100 to 114 kg/ton. The measured values are given in Table 2.

TABLE 2

The influence of the pH value on the efficiency of the addition of aluminium sulphate

| | | 1 | 2 | 3 | 4 |
|---|---|---|---|---|---|
| Aluminium sulphate | kg/ton | 114 | 114 | 114 | 114 |
| pH in stock | | 4.1 | 6.0 | 8.0 | 10.0 |
| Surface weight | g/m² | 825 | 854 | 861 | 849 |
| Thickness | mm | 1.54 | 1.57 | 1.56 | 1.63 |
| Density | kg/m³ | 536 | 544 | 552 | 521 |
| Ash content | % | 0.32 | 2.4 | 2.4 | 1.0 |
| Defibration energy | kJ/kg | 145 | 101 | 144 | 159 |
| Absorption SCAN | | | | | |
| Specific volume | dm³/kg | 21.2 | 20.4 | 21.0 | 21.2 |
| Wet specific volume | dm³/kg | 7.8 | 7.1 | 7.6 | 7.8 |
| Absorption time | s | 2.6 | 2.1 | 2.1 | 2.1 |
| Absorption capacity | g/g | 9.2 | 8.4 | 9.1 | 9.2 |
| Knot content | % | 8.6 | 3.2 | 7.1 | 12.0 |

From Table 2 can be concluded that the retention of aluminium of the fibres in the form of measured ash content, and that particularly the defibration energy and the knot content are strong pH related. This is also shown graphically in FIG. 4.

Figure 4:
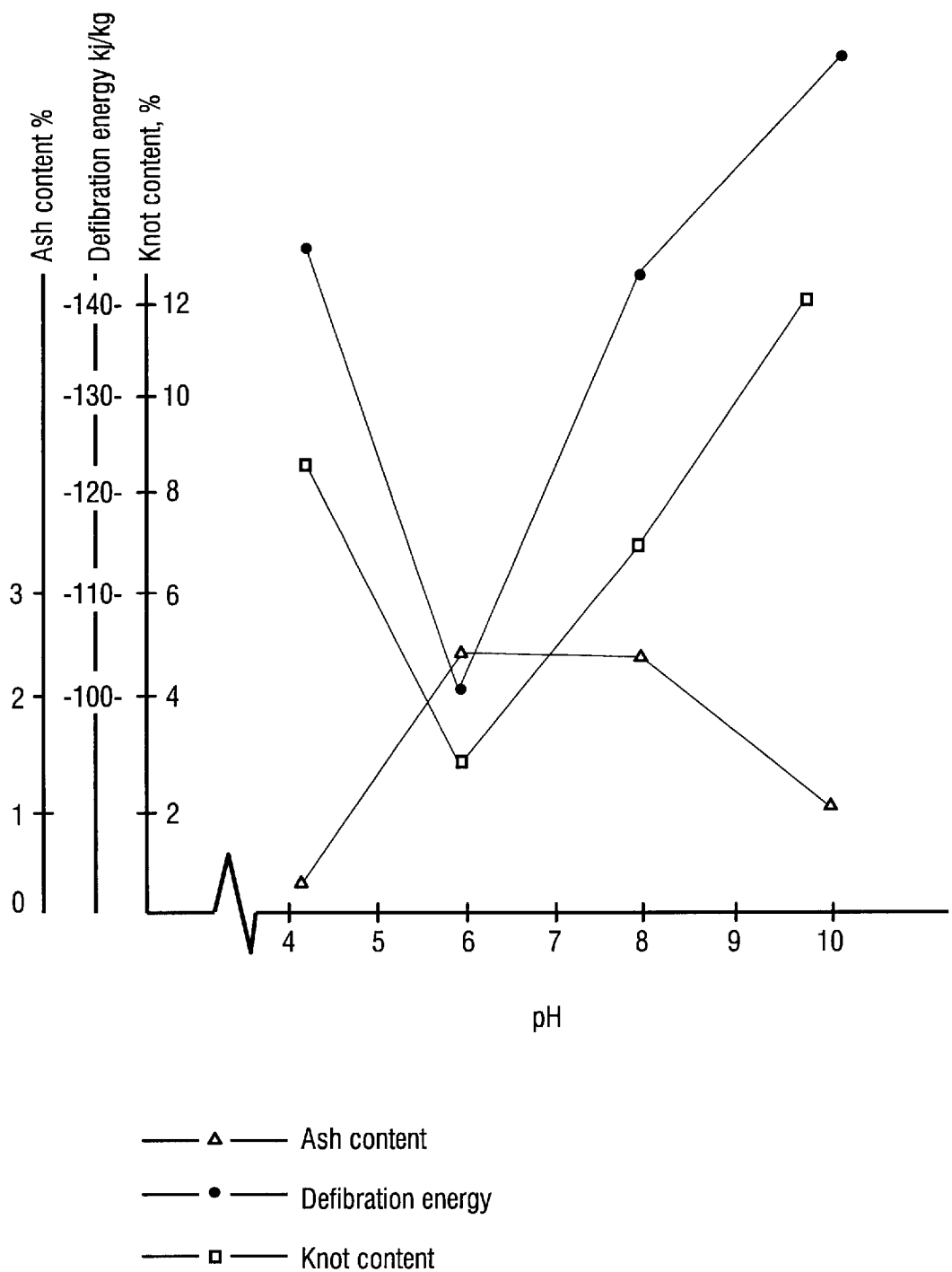
FIG. 4 shows the dependency of the ash content, the defibration energy and the knot content, of the pH value at the treatment with aluminium salt.

From Table 4 and from FIG. 4 can also be concluded that no correspondence to the improved defibration properties of fluff pulp sheets, which have been sheeted at pH 6 to 7, has been noticed at lower and higher pH values. *Paper Chemistry, An introduction,* Dan Eklund, Ton Lindström, DT Paper Science Publications, p 134–144 reports investigations which show that aluminium, originating from water-soluble aluminium salts, exists in the form of different hydroxycomplexes at 4<pH<8, preferably at pH 5 to 7, see FIG. 5. The presence of these complexes in connection with the sheeting of the sheet seems to be a prerequisite for the achievement of an improved defibration result, which indicates the also other, non-polymeric aluminium salts that aluminium sulphate, as for example aluminium nitrate, aluminium hydroxide, aluminium oxyhydroxide, aluminium oxychloride, or other salts of non-polymeric aluminium compounds, which can be dissolved in acid or alkali such that, at the subsequent pH adjustment to the pH range 4<pH<8, preferably pH 5 to 7, the above mentioned active aluminium complexes are established, can be expected to give the desired improvement of the defibration ability. This assumption is also supported by the fact that the ratio aluminium/sulphur in the sheets is substantially higher than in aluminium sulphate, which indicates that it is the said aluminium hydrocomplexes rather than the sulphate ions which are the active parts in the dissolved salt, see Table 4 below. Without binding the invention to any particular theory, the effect upon defibration ability possibly can be explained therein that aluminium hydrocomplexes bind to charged groups in cellulose, hemi-cellulose and lignin residues, which has impact upon the capacity of the fibre-to-fibre binding capacity of the fibres.

Experiments also were performed in order to test the possible effect of other water-soluble salts than aluminium salts—$Na_2SO_4$, $CaCl_2$ and $FeCl_3$—upon the defibration properties. As is evident from Table 3, it could not be noticed that these salts have any impact upon the binding capacity of the fibres in the form of reduced defibration energy and knot content or increased network strength at an ash content of about 2 to 4% in the sheet.

TABLE 3

Investigation of the influence of other salts upon absorption properties, defibration energy, network strength and knot content

|  |  | 1 Reference | 2 | 3 | 4 |
|---|---|---|---|---|---|
| Chemical |  |  | $Na_2SO_4$ | $CaCl_2$ | $FeCl_3$ |
| pH in stock |  | 6.5 | 6.4 | 6.5 | 6.5 |
| Ash content 575° C. | % | 0.20 | 2.53 | 2.89 | 4.8 |
| Surface weight | g/m² | 834 | 847 | 872 | 914 |
| Thickness | mm | 1.50 | 1.59 | 1.61 | 1.60 |
| Density | kg/m³ | 555 | 533 | 542 | 570 |
| Defibration energy, 3500 rpm | kJ/kg | 151 | 145 | 153 | 162 |
| Absorption SCAN |  |  |  |  |  |
| Specific volume | dm³/kg | 20.4 | 20.3 | 19.8 | 19.8 |
| Wet specific volume | dm³/kg | 7.7 | 7.6 | 7.5 | 7.7 |
| Absorption time | s | 2.4 | 2.5 | 2.5 | 1.8 |

TABLE 3-continued

Investigation of the influence of other salts upon absorption properties, defibration energy, network strength and knot content

|  |  | 1 Reference | 2 | 3 | 4 |
|---|---|---|---|---|---|
| Absorption capacity | g/g | 9.2 | 8.9 | 8.7 | 9.1 |
| Network strength | N/lg | 7.0 | 7.1 | 6.7 | 6.4 |
| Knot content | % | 9.9 | 9.7 | 9.9 | 12.1 |

In order to verify the reproducibility of the achieved results when the invention is applied at a larger scale and also for the evaluation of the properties of absorption bodies manufactured from the fluff pulp treated according to the invention, a series of tests were then carried out at a pilot scale.

The pulp which was used during these tests consisted of bleached (delignified) fluff pulp manufactured according to the sulphate cellulose method from Nordic coniferous wood. The pulp was delivered as wet pulp from the pulp mill, dry content about 35%. Charges of about 60 kg conceived dry content were weighed, supplied to pulper and slushed at about 2.5% pulp concentration. In the pulp chest the pulp concentration was adjusted to 1.5% and aluminium sulphate was added. pH was adjusted to about 6.5. Thereafter the stock was stirred for 15 min prior to starting the sheet forming. The pulp concentration was kept at about 0.4% in the head box. The speed of the wire was 2.5 m/min and the formed web was dewatered in a single-filt press roll nip to a dry content of about 50%. Drying to 92 to 95% dry content was made on a cylinder dryer. Defibration was carried out in a hammer hammer mill of type Kamas H01 at a rotation speed of 3000 and 3500 rpm, respectively.

All statements concerning addition of aluminium sulphate also during these experiments refer to aluminium sulphate in the form of a commercial product, manufacturer Kemira AB, with about 75% dry content, if not otherwise is stated.

The results are evident from Table 4 and Table 5.

TABLE 4

|  |  | 0 Reference At end | 1 $Al_2(SO_4)_3$ 70 kg/ton At end | 2 $Al_2(SO_4)_3$ 90 kg/ton At start | 3 $Al_2(SO_4)_3$ 90 kg/ton At end | 4 $Al_2(SO_4)_3$ 110 kg/ton At end |
|---|---|---|---|---|---|---|
| Rotation speed of the defibration mill 3000 rpm |  |  |  |  |  |  |
| Surface weight | g/m² | 799 | 801 | 759 | 823 | 796 |
| Thickness | mm | 1.6 | 1.6 | 1.5 | 1.6 | 1.5 |
| Density | kg/m³ | 514 | 502 | 504 | 532 | 523 |
| Defibration energy 3000 rpm | kJ/kg | 108 | 109 | 87 | 101 | 92 |
| Absorption SCAN |  |  |  |  |  |  |
| Specific volume | dm³/kg | 20.99 | 20.97 | 20.55 | 20.83 | 20.09 |
| Wet specific volume | dm³/kg | 7.87 | 7.90 | 7.59 | 76.8 | 7.57 |
| Absorption time | s | 2.7 | 2.0 | 2.0 | 2.0 | 2.0 |
| Absorption capacity | g/g | 9.2 | 9.3 | 8.8 | 9.1 | 8.6 |
| Network strength | N/lg | 8.3* | 8.5 | 8.5* | 8.3* | 9.1* |
| Knot content | % | 11.9 | 6.9 | 4.2 | 3.7 | 2.7 |
| Al in pulp | mg/kg |  |  | 7500 |  |  |
| $SO_4$ in pulp | mg/kg |  |  | 1800 |  |  |
| Ratio $Al_2/SO_4$ ** in pulp |  |  |  | 4.17 |  |  |

*Standard deviation >0.5
**The ratio aluminium/sulphate in aluminium sulphate is 0.19

TABLE 5

| Rotation speed of the defibration mill 3500 rpm | | 0 Reference At end | 1 $Al_2(SO_4)_3$ 70 kg/ton At end | 2 $Al_2(SO_4)_3$ 90 kg/ton At start | 3 $Al_2(SO_4)_3$ 90 kg/ton At end | 4 $Al_2(SO_4)_3$ 110 kg/ton At end |
|---|---|---|---|---|---|---|
| Surface weight | g/m² | 801 | 812 | 770 | 805 | 821 |
| Thickness | mm | 1.5 | 1.5 | 1.5 | 1.5 | 1.6 |
| Density | kg/m³ | 527 | 546 | 509 | 534 | 521 |
| Defibration energy 3500 rpm | kJ/kg | 129 | 122 | 107 | 117 | 118 |
| Absorption SCAN | | | | | | |
| Specific volume | dm³/kg | 20.83 | 21.42 | 20.79 | 20.90 | 20.89 |
| Wet specific volume | dm³/kg | 7.85 | 7.90 | 7.64 | 7.81 | 7.69 |
| Absorption time | s | 2.6 | 2.1 | 2.1 | 2.2 | 2.1 |
| Absorption capacity | g/g | 9.9 | 9 3 | 8.85 | 9.2 | 8.8 |
| Network strength | N/lg | 7.9 | 7.9* | 9.1* | 8.2 | 8.6 |
| Knot content | % | 7.1 | 6.6 | 3.4 | 4.5 | 4.2 |

*Standard deviation >0.5

From Table 4 and Table 5 is evident that the improvements concerning defibration energy and knot content, which were noticed at laboratory scale and which have been reported in the foregoing, also were achieved in the pilot plant under conditions similar to those of full-scale production. The reduction of the knot content is also illustrated graphically in FIG. 6 and FIG. 7. Particularly FIG. 7 illustrates the reduction of consumed defibration energy in relation to the same defibration result registered as knot content.

Fluff treated with aluminium sulphate also has a higher network strength in consideration of the lower knot content, see particularly Table 5. This is considered to be a very substantial improvement, as there is a trend to use a reduced content of fluff pulp in diapers and other hygiene products. Therefore, the strength (network strength) in the absorption body is increasingly important.

Absorption bodies, as for example diapers, sanitary towels, incontinence products and similar hygiene articles, increasingly often are used in the compressed state, which implies densities larger than 150 kg/m³, and to a larger extent with the addition of some super absorbing product (SAP). Therefore, it is of essential importance, as far as the absorption properties of the fluff pulp are concerned, how the pulp functions in its compressed condition, i.e. when it has been compressed to a high density, and in the presence of SAP. In Table 6 is shown that the fluff pulp, which has been treated with aluminium sulphate, in its compressed condition and in combination with super absorbing product (SAP=Favor SXM 75, trade-name), gets a significantly increased absorbency rate, in comparison with the non-aluminium sulphate treated but SAP-containing reference pulp, and that the rewetting is significantly reduced, in one case with 41%, mean value 30%.

TABLE 6

Absorbency rate and rewetting; density appr 320 kg/m³

| Rotation speed of the defibration mill 3500 rpm | | 0 Reference At end | 1 $Al_2(SO_4)_3$ 70 kg/ton At end | 2 $Al_2(SO_4)_3$ 90 kg/ton At end | 3 $Al_2(SO_4)_3$ 110 kg/ton At end |
|---|---|---|---|---|---|
| Surface weight, guide value | g/m² | 1000 | 1000 | 1000 | 1000 |
| Surface weight SAP, guide value | g/m² | 140 | 140 | 140 | 140 |
| Sample weight incl SAP (12 × 30 cm) | g | 39.6 | 41.2 | 39.6 | 41.5 |
| Volume SAP | g | 5 | 5 | 5 | 5 |
| Surface weight, (fluff + SAP) | g/m² | 1137 | 1184 | 1138 | 1185 |
| Thickness (fluff + SAP) | mm | 3.6 | 3.6 | 3.6 | 3.6 |
| Density (fluff + SAP) | kg/m³ | 317 | 326 | 320 | 331 |
| Absorbency rate 4 × 50 ml | | | | | |
| Dosage 1 | ml/s | 0.97 | 1.29 | 1.21 | 1.18 |
| Dosage 2 | ml/s | 0.65 | 0.82 | 0.82 | 0.88 |
| Dosage 3 | ml/s | 0.41 | 0.58 | 0.57 | 0.57 |
| Dosage 4 | ml/s | 0.25 | 0.36 | 0.31 | 0.35 |
| Rewetting -200 ml | g | 6.3 | 3.8 | 5.8 | 3.7 |
| Reduction of rewetting | % | | 40 | 8 | 41 |

SAP = Favor SXM 75. The test samples are made in dry sheet molds

In the Table 7 below, the results for test samples which have been compressed to dry density of appr. 170 kg/m³ are reported. From this table it is evident that the relative increase of absorbency rate is substantially smaller as compared with comparable samples with higher density. The increase is only 6% and is possibly not significant, as the reference sample has a somewhat lower total weight than the test samples. The rewetting, however, is improved in a similar was as for compressed samples.

TABLE 7

Absorbency rate and rewetting; density appr 170 kg/m$^3$

| Rotation speed of the defibration mill 3500 rpm | | 0 Reference | 1 Al$_2$(SO$_4$)$_3$ 70 kg/ton | 2 Al$_2$(SO$_4$)$_3$ 90 kg/ton | 3 Al$_2$(SO$_4$)$_3$ 110 kg/ton |
|---|---|---|---|---|---|
| Surface weight; guide value | g/m$^2$ | 1000 | 1000 | 1000 | 1000 |
| Surface weight SAP; guide value | g/m$^2$ | 140 | 140 | 140 | 140 |
| Sample weight incl. SAP (12 × 30 cm) | g | 37.8 | 40.2 | 39.3 | 41.7 |
| Volume SAP | g | 5 | 5 | 5 | 5 |
| Surface weight, (fluff + SAP) | g/m$^2$ | 1135 | 1163 | 1153 | 1205 |
| Thickness (fluff + SAP) | mm | 6.9 | 6.9 | 7.1 | 7.1 |
| Density (fluff + SAP) | kg/m$^3$ | 165 | 170 | 163 | 171 |
| Absorbency rate 4 × 50 ml | | | | | |
| Dosage 1 | ml/s | 2.81 | 2.44 | 2.27 | 2.17 |
| Dosage 2 | ml/s | 1.10 | 1.06 | 1.06 | 1.01 |
| Dosage 3 | ml/s | 0.72 | 0.71 | 0.74 | 0.69 |
| Dosage 4 | ml/s | 0.49 | 0.52 | 0.54 | 0.52 |
| Rewetting - 200 ml | g | 7.4 | 2.4 | 3.8 | 1.7 |

SAP = Favor SXM 75. The test samples are made in dry sheet molds

The shorter absorption time according to SCAN was verified through investigation of absorption time for test samples made of chemical pulp without change of volume, wherein the test sample was compressed in its dry state to bulk 7.1 dm$^3$/kg. The purpose with this test was to eliminate possible effects because of the fact that the fluff body changes its dimensions when being wetted. The result is shown in Table 8. The result possibly can be interpreted as an increased wettability of the chemical pulp fibres, but any corresponding increase of the absorbency rate was not noticed as the investigation of the absorption process on inclined plane, see FIG. 3B. The true causes of the result thus are not clear, since the samples also have different degree of separation of the fibres, which complicates the interpretation.

TABLE 8

| Sample | Absorption time s | Absorption capacity g/g |
|---|---|---|
| Ref | 1.2 | 8.3 |

TABLE 8-continued

| Sample | Absorption time s | Absorption capacity g/g |
|---|---|---|
| Al$_2$(SO$_4$)$_3$, 70 kg/ton | 1.0 | 8.3 |
| Al$_2$(SO$_4$)$_3$, 110 kg/ton | 1.0 | 8.3 |

Experiments also were carried out of additions of polyaluminium chloride to the stock at pH 6.5 The experiments are reported in Table 9, which shows that the addition of this aluminium salt had a negative impact upon the defibration ability. Knot content as well as defibration energy increased, which indicates that the desired effect of the invention in terms of defibration ability, which was achieved when the fibres had been treated with an aluminium salt at pH 6 to 7, is achieved only under the condition that the aluminium salt or salts is/are any non polymeric aluminium salt, which is soluble in water.

TABLE 9

Tests with polyaluminium chloride

| | | 0 Reference | 1 | 2 | 3 | 4 |
|---|---|---|---|---|---|---|
| Polyaluminium chloride (PAX - 14) | kg/ton | 0 | 25 | 50 | 75 | 75 |
| pH | | 6.4 | 6.5 | 6.4 | 6.4 | 5.4 |
| Amount 1 M HCl*/5 M NaOH | ml | 1.3* | 1.2 | 2.6 | 4.2 | 3.8 |
| Ash content (575°) | % | 0.29 | 0.57 | 0.98 | 1.32 | 1.26 |
| Surface weight | g/m$^2$ | 817 | 820 | 815 | 860 | 832 |
| Thickness | mm | 1.5 | 1.5 | 1.5 | 1.6 | 1.6 |
| Density | kg/m$^3$ | 540 | 548 | 529 | 536 | 524 |
| Defibration energy 3500 rpm | kJ/kg | 147 | 164 | 175 | 184 | 182 |
| Absorption SCAN | | | | | | |
| Specific volume | dm$^3$/kg | 20.81 | 21.07 | 21.06 | 20.68 | 20.62 |
| Wet specific volume | dm$^3$/kg | 7.79 | 8.96 | 8.04 | 8.10 | 7.85 |
| Absorption time | s | 2.7 | 2.7 | 2.5 | 2.3 | 2.2 |
| Absorption capacity | g/g | 9.3 | 9.3 | 9.6 | 9.4 | 9.4 |
| Knot content | % | 8.3 | 15.6 | 18.2 | 22.0 | 19.4 |

A miner test also was made on chemo-thermomechanical pulp, CTMP, with the addition of aluminium sulphate, pH≈6.5. A significant influence on the defibration energy was noticed only for the highest level of dosage of aluminium sulphate, 130 kg/ton, Table 10. Any significant influence on the defibration result in the form of increased network strength, however, could not be noticed, but there was achieved a high retention of aluminium and a substantial reduction of the absorption time, from 7.8 to 2.5 s.

TABLE 10

Tests with CTMP-additions of debonder and aluminium sulphate, respectively

| FF 950154: | | 0 Reference | 1 | 2 | 3 | 4 | 5 |
|---|---|---|---|---|---|---|---|
| Aluminium sulphate | kg/ton | | | 50 | 75 | 100 | 130 |
| Berocell 509 | kg/ton | | 3 | | | | |
| pH | | 6.6–6.7 | 6.5–6.7 | 6.4–6.5 | 6.5–6.6 | 6.4–6.6 | 6.4–6.5 |
| Aluminium content, sheet | mg/kg | 12 | 11 | 4000 | 6100 | 7800 | 1000 |
| Aluminium content, white water | mg/l | <0.5 | <0.5 | 0.9 | 1.2 | 1.6 | 0.7 |
| Surface weight | g/m$^2$ | 640 | 635 | 644 | 661 | 668 | 666 |
| Thickness | mm | 2.2 | 2.5 | 2.2 | 2.1 | 2.2 | 1.9 |
| Density | kg/m$^3$ | 292 | 255 | 299 | 313 | 310 | 351 |
| Defibration energy 3500 rpm | kJ/kg | 87 | 77 | 96 | 94 | 86 | 72 |
| Absorption SCAN | | | | | | | |
| Specific volume | dm$^3$/kg | 19.14 | 18.39 | 18.98 | 18.63 | 18.28 | 17.50 |
| Wet specific volume | dm$^3$/kg | 8.24 | 8.18 | 8.46 | 8.29 | 8.25 | 8.20 |
| Absorption time | s | 7.6 | 6.6 | 4.6 | 3.2 | 2.8 | 2.5 |
| Absorption capacity | g/g | 9.3 | 9.2 | 9.6 | 9.4 | 9.2 | 9.1 |
| Network strength | N/lg | 6.4 | 6.2 | 6.2 | 6.2 | 6.3 | 6.3 |

The improved defibration properties can be employed also when aluminium sulphate treated cellulose fibres are combined with a certain amount, 0 to 20%, of synthetic reinforcing fibres of e.g. rayon, polyester, polypropylene, polyethylene or so called binding fibres which are activated by heating. A good defibration result, with a low knot content, can be obtained with widely open screen in a hammer mill and also without any screen.

The above examples illustrate the high capacity of aluminium complexes formed in an aqueous solution adjusted to 4<pH<8 to improve the defibration properties of fluff pulp, and particularly chemical fluff pulp. The improved defibration properties provide possibilities to increase strength and to obtain a lower knot content in the defibrated material. These improvements of chemical pulp are achieved with maintained or to some extent improved wettability of the fibres.

What is claimed is:

1. A method of preparing fluffed pulp for the manufacture of absorbent material which is to be used as a component in absorbent products, comprising the steps of:
   adjusting the pH of a stock, which consists essentially of bleached chemical pulp consisting of cellulosic fibres in aqueous suspension, to 4<pH<8;
   adding at least one water-soluble, non-polymeric aluminium salt to the stock, said salt in aqueous solution at said pH forming at least one hydrocomplex with aluminium of the type Al(OH)$_n^x$, where n is a number between 1 and 3, and x is 0, + or 2+;
   causing said slat in aqueous solution to act on the cellulosic fibres in said suspension at said pH during a period of time of at least 2 min; and
   forming the fibre pulp thereafter into a web, which is dewatered and dried, in which fibre pulp the fibres are separated through defibration in dry state of the pulp, by a supply of defibration energy not exceeding 130 kg/kg dry substance, giving a network strength of at least 7 N/g to form a fluffed pulp.

2. A method according to claim 1, wherein said hydrocomplex is one or more of the complexes which comprises Al(OH)$_3^0$, Al(OH)$_2^+$ and Al(OH)$^{2+}$.

3. A method according to claim 1, wherein the stock is adjusted to a pH between 5 and 7.

4. A method according to claim 3, wherein the stock is adjusted to a pH between 5.5 and 6.5

5. A method according to claim 1, wherein said salt in aqueous solution is caused to act on the cellulosic fibres at said pH during a period of time of 5 to 60 min.

6. A method according to claim 1, wherein said salt consists of at least of any of the salts belonging to the group consisting of aluminum sulphate, aluminium nitrate, aluminium hydroxide, aluminiumoxy hydroxide, aluminiumoxy chloride and other salts of non-polymeric aluminium compounds which can be dissolved in acid or alkali to form said active aluminium hydrocomplexes.

7. A method according to claim 4, wherein the salt is aluminium sulphate.

8. A method according to claim 1 wherein said at least one water-soluble, non-polymeric aluminum salt is added to the stock in amount corresponding to 3–24 gAl/kg pulp.

9. A method according to claim 8, wherein the amount of non-polymeric aluminium salt corresponds to 6–12 gAl/kg pulp.

10. A method according to claim 1, wherein the cellulosic pulp is bleached cellulose pulp manufactured according to the sulfate cellulose method.

11. A method according to claim 1, wherein the separated fibers have a knot content of max. 8%.

12. A method according to claim 1, wherein the separated fibers have a knot content of max. 7%.

13. A method according to claim 1, wherein said supply of defibration energy does not exceed 120 kj/kg dry substance.

14. A method according to claim 1, wherein the defibrated material has a net work strength of at least 8.0 N/g.

15. A method according to claim 1, wherein the defibrated material has a knot content of max. 8% and a net work strength of at least 8.0 N/g.

* * * * *